(12) United States Patent
Sakata (10) Patent No.: US 10,226,222 B2
(45) Date of Patent: Mar. 12, 2019

(54) X-RAY DIAGNOSTIC APPARATUS AND FOOT SWITCH USED FOR THE SAME

(71) Applicant: Toshiba Medical Systems Corporation, Otawara-shi (JP)

(72) Inventor: Mitsuru Sakata, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 128 days.

(21) Appl. No.: 14/737,065

(22) Filed: Jun. 11, 2015

(65) Prior Publication Data

US 2015/0305694 A1 Oct. 29, 2015

Related U.S. Application Data

(63) Continuation of application No. PCT/JP2013/083215, filed on Dec. 11, 2013.

(30) Foreign Application Priority Data

Dec. 11, 2012 (JP) .................. 2012-270847

(51) Int. Cl.
*A61B 6/10* (2006.01)
*A61B 6/04* (2006.01)
(Continued)

(52) U.S. Cl.
CPC ............ *A61B 6/102* (2013.01); *A61B 6/0407* (2013.01); *A61B 6/4441* (2013.01); *A61B 6/547* (2013.01);
(Continued)

(58) Field of Classification Search
CPC .............................. A61B 6/4405; A61B 6/548
See application file for complete search history.

(56) References Cited

U.S. PATENT DOCUMENTS 6,007,243 A * 12/1999 Ergun ................... A61B 6/548
348/E5.081
6,131,690 A * 10/2000 Galando .............. A61B 6/4405
180/19.1
(Continued)

FOREIGN PATENT DOCUMENTS

JP 06-261893 A 9/1994
JP 09-084000 A 3/1997
(Continued)

OTHER PUBLICATIONS

International Search Report dated Jan. 28, 2014 in PCT/JP2013/083215 filed Dec. 11, 2013.
(Continued)

*Primary Examiner* — Hoon K Song
(74) *Attorney, Agent, or Firm* — Oblon, McClelland, Maier & Neustadt, L.L.P.

(57) ABSTRACT

According to one embodiment, an X-ray diagnostic apparatus which can improve operability is provided. This apparatus comprises a top configured to move, a bed including the top, an X-ray tube configured to generate X-rays applied to an object placed on the top, a peripheral unit used around the bed, and control processing circuitry configured to generate a control signal. The peripheral unit moves in a self-propelled manner between a first position and a second position by a motor. The control processing circuitry generates a control signal for controlling the movement of the peripheral unit.

13 Claims, 6 Drawing Sheets

(51) Int. Cl.
    *A61B 6/00*     (2006.01)
    *A61B 6/02*     (2006.01)

(52) U.S. Cl.
    CPC .................. *A61B 6/56* (2013.01); *A61B 6/02* (2013.01); *A61B 6/107* (2013.01); *A61B 6/481* (2013.01); *A61B 6/542* (2013.01)

(56) References Cited

U.S. PATENT DOCUMENTS

| | | | |
|---|---|---|---|
| 2002/0085682 A1* | 7/2002 | Noegel | A61B 6/4405 378/198 |
| 2004/0076262 A1* | 4/2004 | Shao | A61B 6/037 378/196 |
| 2006/0203250 A1* | 9/2006 | Regn | A61B 6/00 356/482 |

FOREIGN PATENT DOCUMENTS

| | | |
|---|---|---|
| JP | 2001-046365 A | 2/2001 |
| JP | 2007-044353 A | 2/2007 |
| JP | 2010-082431 A | 4/2010 |
| JP | 2011-030686 A | 2/2011 |
| JP | 2011-217904 A | 11/2011 |

OTHER PUBLICATIONS

International Written Opinion dated Jan. 28, 2014 in PCT/JP2013/083215 filed Dec. 11, 2013 with English translation.

\* cited by examiner

X-RAY DIAGNOSTIC APPARATUS AND FOOT SWITCH USED FOR THE SAME

CROSS-REFERENCE TO RELATED APPLICATIONS

This application is a Continuation application of PCT Application No. PCT/JP2013/083215, filed Dec. 11, 2013 and based upon and claiming the benefit of priority from the Japanese Patent Application No. 2012-270847, filed Dec. 11, 2012, the entire contents of which are incorporated herein by reference.

FIELD

Embodiments described herein relate generally to an X-ray diagnostic apparatus used for the diagnosis and medical treatment of an object and a foot switch used for the X-ray diagnostic apparatus.

BACKGROUND

Recently, along with the development of intervention using catheters, X-ray diagnostic apparatuses have progressed mainly in the circulatory organ field. There has been developed a hybrid system constituted by such an X-ray diagnostic apparatus for circulatory organs and a surgical bed which are combined to enable an intervention treatment or surgical treatment.

Figure 6:
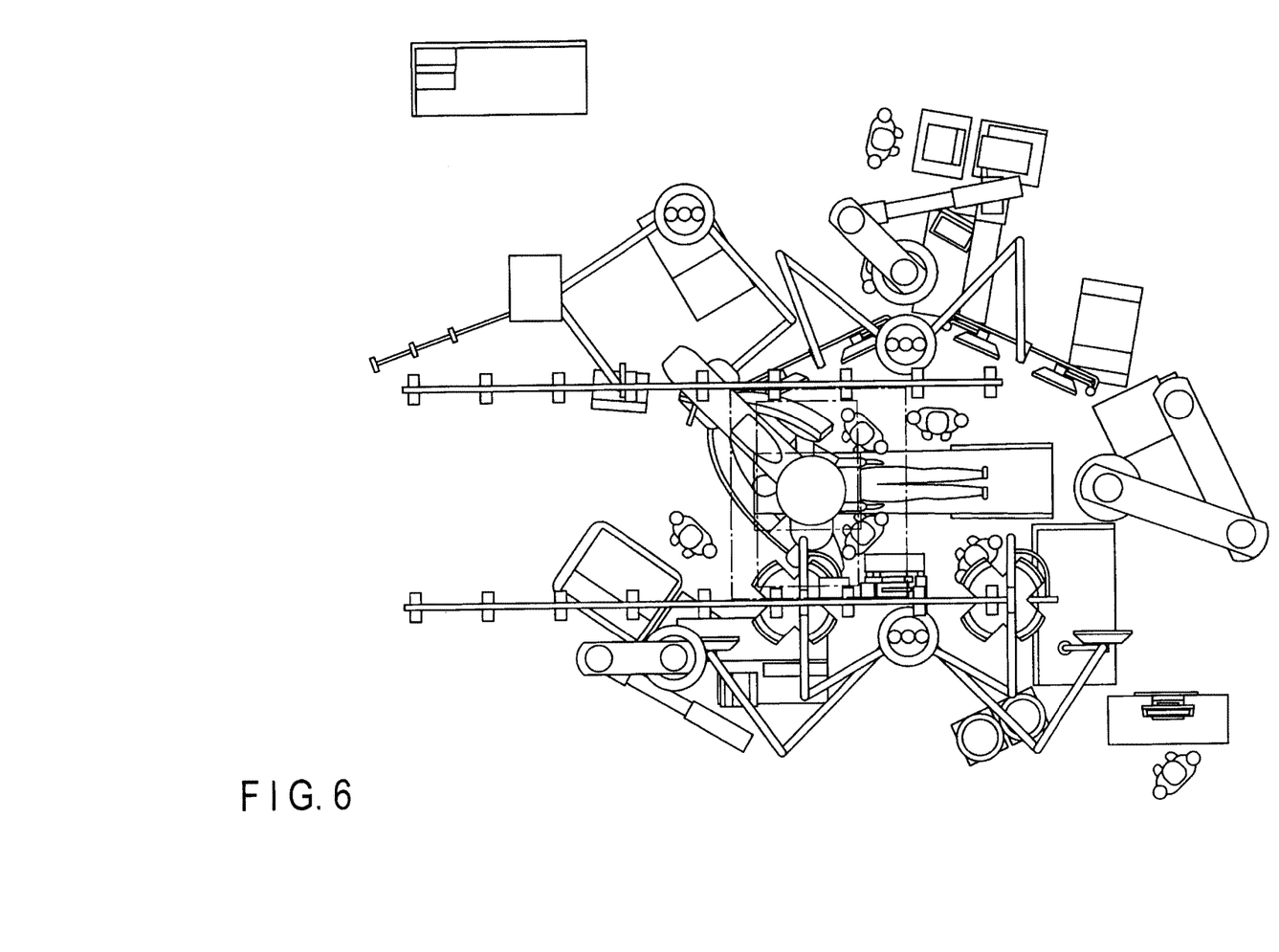
FIG. 6 is a view showing an imaging room in which a hybrid system is installed, when viewed from above.

FIG. 6 is a view showing an imaging room in which a hybrid system is installed, when viewed from above. As shown in FIG. 6, according to the hybrid system, there are provided, around a bed installed in an imaging room, various units used for an intervention treatment or surgical treatment (for example, a C-arm having an imaging system, its driving mechanism, a bed moving mechanism, a display unit suspended from the ceiling, a display unit placed on the floor, a console and foot switches for inputting various types of inputs, a mount table for medical instruments, and an ultrasonic diagnostic apparatus). In such an environment, a plurality of persons including a doctor and nurse perform a medical treatment. For this reason, an unoccupied floor area around the bed is small. This interferes with an operation by an internist, surgeon, or the like. Under the circumstances, an attempt has been made to increase the unoccupied area around a bed by replacing a peripheral unit of an X-ray diagnostic apparatus, e.g., a foot switch, which is placed around the bed with a wireless foot switch without any cable.

Although the occupied area of the peripheral unit decreases by the absence of a cable, the unit cannot be used, once the internal battery runs out, until it is recharged. This makes it impossible for the operator to use the unit immediately when he/she wants to use it. In addition, if a given peripheral unit can be used for only one type of medical treatment, the operator needs to move the unit to a place where it does not interfere with his/her operation while he/she does not use it.

An embodiment has been made to solve the above problem and has as its object to provide an X-ray diagnostic apparatus which can improve operability and a foot switch used in the X-ray diagnostic apparatus.

DETAILED DESCRIPTION

According to one embodiment, an X-ray diagnostic apparatus which can improve operability is provided. This apparatus comprises a top configured to move, a bed including the top, an X-ray tube configured to generate X-rays applied to an object placed on the top, a peripheral unit used around the bed, and control processing circuitry configured to generate a control signal. The peripheral unit moves in a self-propelled manner between a first position and a second position by a motor. The control processing circuitry generates a control signal for controlling the movement of the peripheral unit.

An embodiment will be described below with reference to the accompanying drawings.

Figure 1:
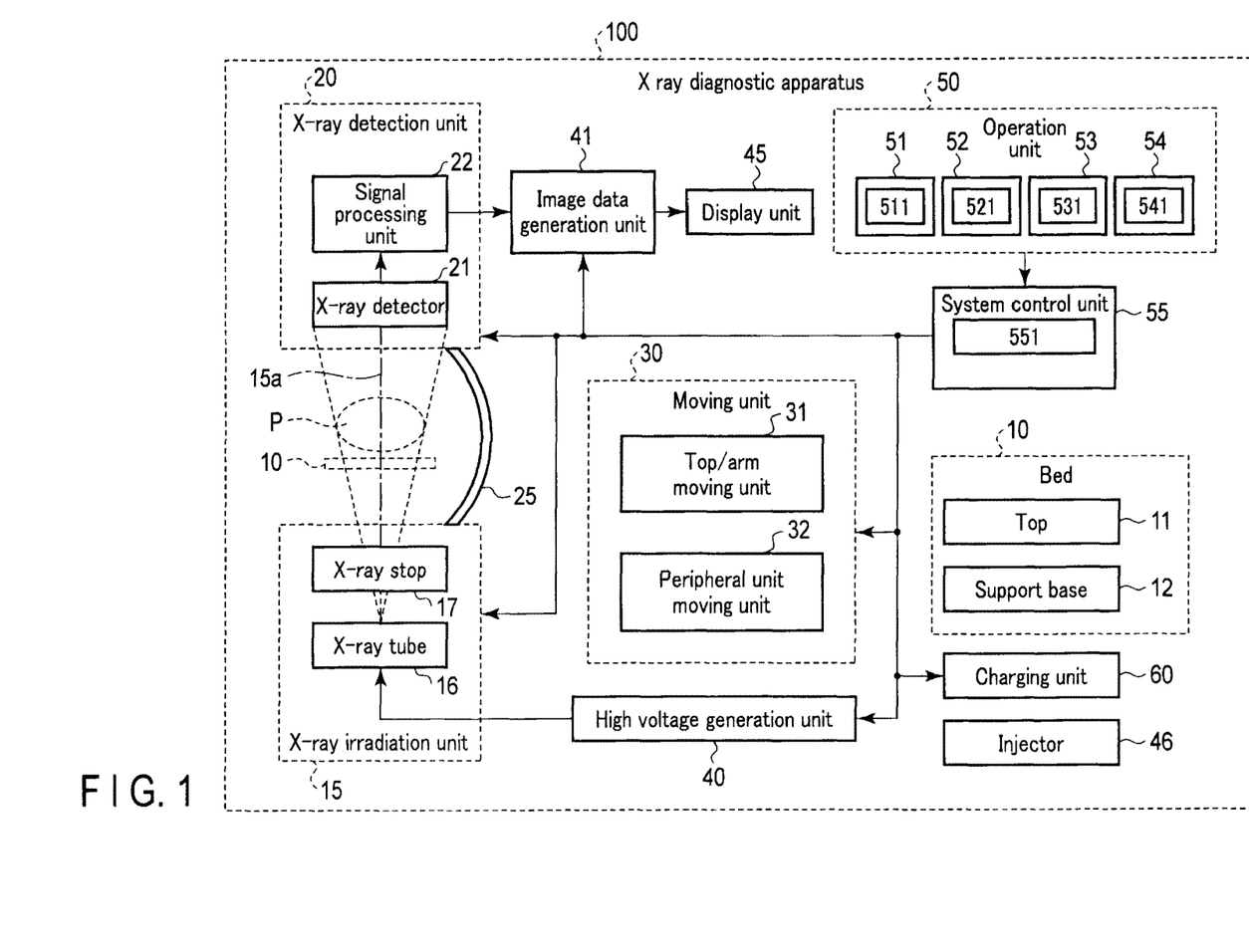
FIG. 1 is a block diagram showing the arrangement of an X-ray diagnostic apparatus according to an embodiment.

FIG. 1 is a block diagram showing the arrangement of an X-ray diagnostic apparatus. An X-ray diagnostic apparatus 100 includes a bed 10 on which an object P is placed, and an X-ray irradiation unit 15 (X-ray source) which irradiates the object P placed on the bed 10 with X-rays. The X-ray diagnostic apparatus 100 also includes an X-ray detection unit (X-ray detector) 20 which detects the X-rays emitted by the X-ray irradiation unit 15 and transmitted through the object P and an arm 25 which holds the X-ray irradiation unit 15 and the X-ray detection unit 20.

In addition, the X-ray diagnostic apparatus 100 includes a moving unit 30 (motor) which moves the bed 10, the X-ray irradiation unit 15, the X-ray detection unit 20, and the like and a high voltage generation unit 40 (high voltage generator) which drives the X-ray irradiation unit 15 to emit X-rays. The X-ray diagnostic apparatus 100 further includes an image data generation unit 41 (image data generation circuitry) which generates image data based on the signal detected by the X-ray detection unit 20 and a display unit 45 (display) which displays the image data generated by the image data generation unit 41.

Furthermore, the X-ray diagnostic apparatus 100 includes an injector 46 for injecting a contrast medium into the object P placed on the bed 10 and an operation unit 50 which, for example, inputs various types of commands. The X-ray diagnostic apparatus 100 also includes a charging unit 60 (charging circuitry) which supplies power (control circuitry) to some units of the moving unit 30 and a system control unit 55 which controls the respective units described above based on input information input from the operation unit 50.

The bed 10 includes a top 11 and a top support base 12. The top 11 is placed in the imaging room covered with a shield member which prevents X-rays from leaking outside.

The object P is placed on the top 11. The top support base 12 movably supports the top 11.

The X-ray irradiation unit 15 includes an X-ray tube 16 and an X-ray stop 17. The X-ray tube 16 generates X-rays applied to the object P for fluoroscopy and X-rays for imaging, which have higher energy than those for fluoroscopy. The X-ray stop 17 controls the aperture of the irradiation opening through which X-rays from the X-ray tube 16 pass.

The X-ray detection unit 20 includes an X-ray detector 21 and a signal processing unit 22. The X-ray detector 21 detects the X-rays emitted by the X-ray irradiation unit 15 though the X-ray stop 17 and transmitted through the object P. The signal processing unit 22 generates X-ray projection data based on the signal detected by the X-ray detector 21.

The moving unit 30 includes a top/arm moving unit 31 and a peripheral unit moving unit 32. The top/arm moving unit 31 independently moves the top 11 of the bed 10, the X-ray irradiation unit 15, and the X-ray detection unit 20. The peripheral unit moving unit 32 moves a peripheral unit used by a doctor, nurse, technician, or the like, as needed, around the bed 10 for an examination, intervention treatment, or surgical treatment for the object P placed on the top 11 from one of a use position where he/she can easily use the unit and a retreat position where the unit considered as an unnecessary unit does not interfere with an operation to the other position by moving in a self-propelled manner.

Figure 2:
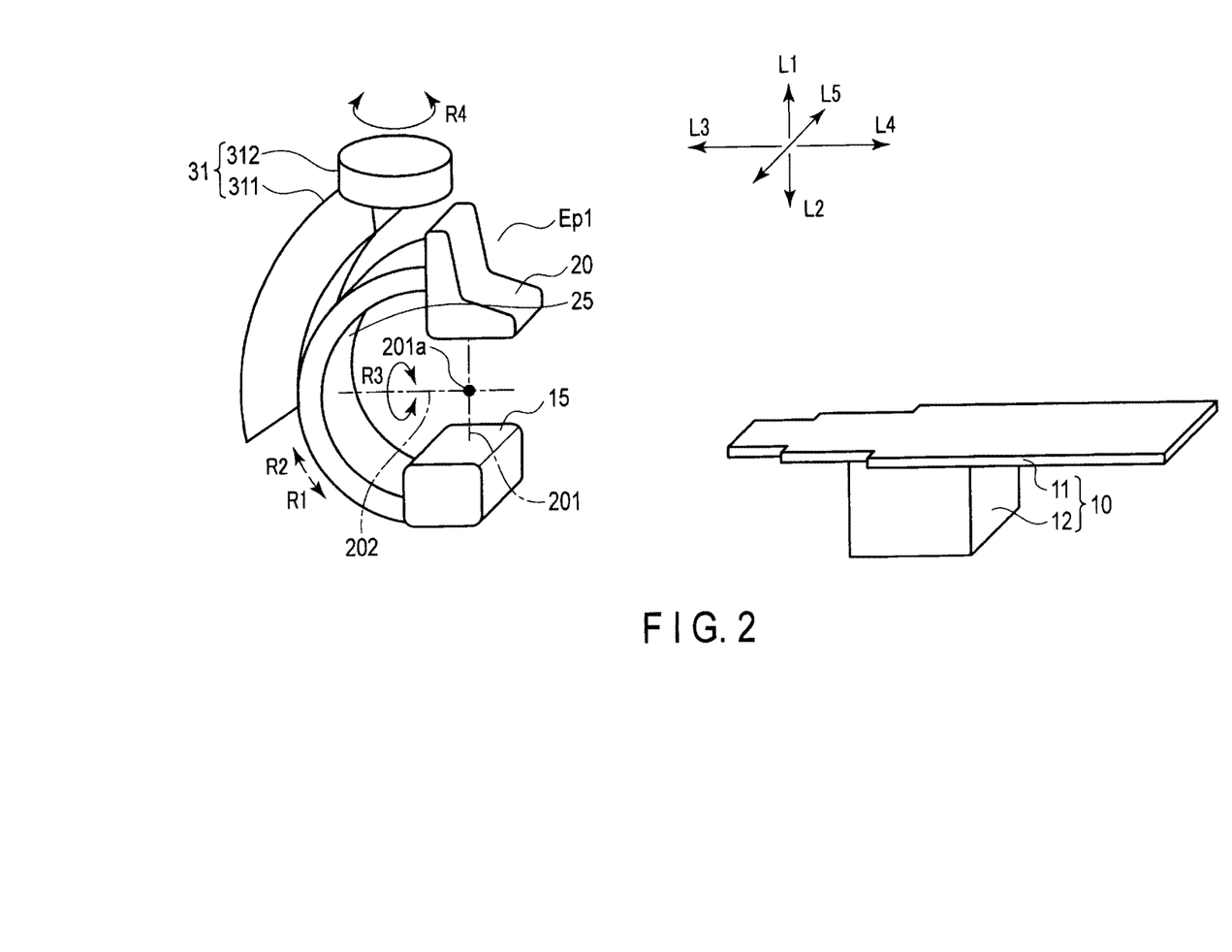
FIG. 2 is a view showing an example of each of the moving directions of a top, X-ray irradiation unit, and X-ray detection unit according to the embodiment.

FIG. 2 is a view showing an example of each of the moving directions of the top 11, X-ray irradiation unit 15, and X-ray detection unit 20.

The top/arm moving unit 31 moves the top 11 in the arrow L1 direction and the arrow L2 direction, which are the vertical directions, the arrow L3 direction and the arrow L4 direction, which are the longitudinal directions, and the arrow L5 direction, which is the widthwise direction. The top/arm moving unit 31 also tilts the top 11 in the longitudinal and widthwise directions.

The top/arm moving unit 31 includes a first support member 311 and a second support member 312. The first support member 311 pivotally supports the arm 25. The second support member 312 is placed near the ceiling in the imaging room and pivotally supports the first support member 311. The top/arm moving unit 31 stops the X-ray irradiation unit 15 and the X-ray detection unit 20 at a retreat position Ep1 away from the bed 10 so as not to interfere with an operation by the operator when X-ray emission is stopped. When the apparatus performs X-ray emission, the top/arm moving unit 31 moves the X-ray irradiation unit 15 and the X-ray detection unit 20 at the retreat position Ep1 in the L4 direction as the direction to approach the bed 10 by moving the second support member 312.

The top/arm moving unit 31 moves the X-ray irradiation unit 15 and the X-ray detection unit 20 to set the direction in which X-rays are applied to the object P placed on the top 11. Assume that in this case, the top/arm moving unit 31 moves the X-ray irradiation unit 15 and the X-ray detection unit 20 in the arrow R1 direction and the arrow R2 direction opposite to the R1 direction by making the arm 25 pivot about a pivot center 201a located on a straight line 201 passing through the center of the X-ray irradiation unit 15 and X-ray detection unit 20.

In addition, the top/arm moving unit 31 moves the X-ray irradiation unit 15 and the X-ray detection unit 20 in the arrow R3 direction by making the arm 25 pivot about a straight line 202 as a pivot axis which is perpendicular to the straight line 201 at the pivot center 201a. The top/arm moving unit 31 further moves the X-ray irradiation unit 15 and the X-ray detection unit 20 in the arrow R4 direction by making the first support member 311 pivot, and moves the X-ray irradiation unit 15 and the X-ray detection unit 20 in the L5 direction by moving the second support member 312. When the apparatus stops X-ray emission, the top/arm moving unit 31 moves the X-ray irradiation unit 15 and the X-ray detection unit 20 in the L3 direction to separate from the bed 10 by moving the second support member 312, and stops them at the retreat position Ep1.

The injector 46 shown in FIG. 1 is a peripheral unit to be used around the bed 10 when the operator performs, for example, an angiographic examination, and includes a cylinder for injecting a contrast medium into the object P placed on the top 11 of the bed 10. The injector 46 moves to a retreat position spaced apart from the bed 10 so as not to interfere with an operation by the operator when the apparatus stops X-ray emission, and moves to a use position around the bed 10 when the apparatus performs X-ray emission upon injection of a contrast medium into the object P.

The operation unit 50 is provided to operate an X-ray diagnostic apparatus 100 and includes a first operation unit 51, a second operation unit 52, a third operation unit 53, and a fourth operation unit 54. The first operation unit 51 is placed in an operation room adjacent to the imaging room. The second operation unit 52 and the third operation unit 53 are arranged in the imaging room so as to be manually movable. The fourth operation unit 54 is placed in the imaging room so as to be movable by the peripheral unit moving unit 32 of the moving unit 30.

The first operation unit 51, the second operation unit 52, and the third operation unit 53 respectively include input units 511, 521, and 531 (input processing circuitry) each including input devices such as a plurality of switches and a display panel. With the first operation unit 51, the second operation unit 52, and the third operation unit 53, the operator performs an input operation for setting X-ray irradiation conditions such as a tube voltage, a tube current, and an irradiation time, an input operation for moving the top 11 of the bed 10, an input operation for moving the X-ray irradiation unit 15 and the X-ray detection unit 20, an input operation for moving a peripheral unit, an input operation for starting X-ray emission, an input operation for stopping X-ray emission, and the like.

The fourth operation unit 54 includes a foot switch 541. With the fourth operation unit 54, the operator performs an input operation for starting X-ray emission and an input operation for stopping X-ray emission.

The charging unit 60 is placed near the peripheral unit moving unit 32 of the moving unit 30 which has moved a peripheral unit to the retreat position. The charging unit 60 supplies power to the peripheral unit moving unit 32 contactlessly by, for example, electromagnetic induction when the peripheral unit is at rest at the retreat position.

The system control unit 55 includes a communication unit 551 which performs wireless communication between the CPU, the storage circuit, and the fourth operation unit 54 of the operation unit 50. The system control unit 55 comprehensively controls the X-ray irradiation unit 15, the X-ray detection unit 20, the moving unit 30, the high voltage generation unit 40, the image data generation unit 41, and the charging unit 60 based on these pieces of input information after the pieces of input information input from the operation unit 50 are temporarily stored.

An example of the arrangement and operation of the third and fourth operation units 53 and 54 of the operation unit 50 and the peripheral unit moving unit 32 of the moving unit 30 which moves the fourth operation unit 54 will be described below.

Figure 3:
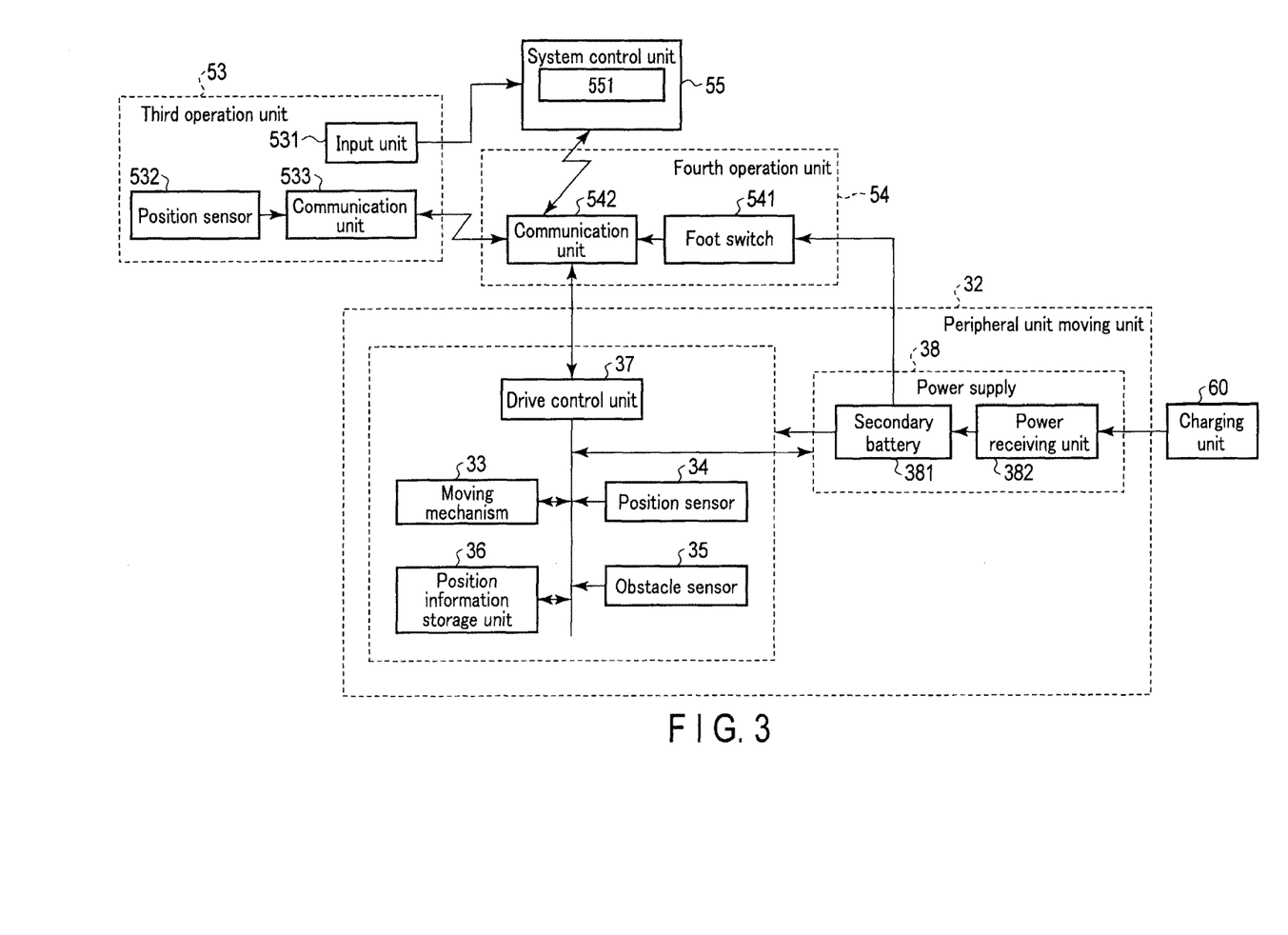
FIG. 3 is a block diagram showing the arrangement of the third and fourth operation units and peripheral unit moving unit according to the embodiment.

FIG. 3 is a block diagram showing the arrangement of the third and fourth operation unit 53 and 54 and the peripheral unit moving unit 32.

The third operation unit 53 includes the input unit 531, a position sensor 532, and a communication unit 533. The input unit 531 includes input devices such as a plurality of switches for operating the X-ray diagnostic apparatus 100 and a display panel. The position sensor 532 includes a receiver which detects the magnetic field generated by a transmitter placed, for example, near the charging unit 60, and detects the position of the input unit 531. The communication unit 533 wirelessly transmits the position of the input unit 531, detected by the position sensor 532, as position information of the third operation unit 53 to the fourth operation unit 54. The third operation unit 53 is then placed around the bed 10. The position of the third operation unit 53 is changed for each examination or medical treatment in consideration of the standing positions of operators such as a doctor, nurse, and technician who use the operation unit.

The fourth operation unit 54 includes the foot switch 541 and a communication unit 542 (a transmitter and a receiver). The foot switch 541 enables to input, for example, an instruction to perform X-ray emission or to stop X-ray emission in accordance with a foot operation. The communication unit 542 performs wireless communication between the communication unit 551 of the system control unit 55 and the communication unit 533 of the third operation unit 53. The communication unit 542 also transmits the input information input from the foot switch 541 to the system control unit 55. The system control unit 55 performs X-ray emission or stop X-ray emission based on the input information input from the foot switch 541.

In addition, the communication unit 542 receives the input information input from one of the first operation unit 51, the second operation unit 52, and the third operation unit 53 and transmitted from the communication unit 551 of the system control unit 55 and the position information of the third operation unit 53 transmitted from the communication unit 533 of the third operation unit 53, and outputs the information to the peripheral unit moving unit 32. The peripheral unit moving unit 32 moves the fourth operation unit 54 based on input information from the system control unit 55 and the position information of the third operation unit 53, which are output from the communication unit 542.

Providing the communication unit 542 in this manner can eliminate the necessity of a communication cable in the imaging room, thereby reducing the floor area occupied by the fourth operation unit 54. This makes it possible to ensure a wide floor area for the installation of peripheral units around the bed 10 and wide passages for operators, thereby improving operability.

The peripheral unit moving unit 32 includes a moving mechanism 33, a position sensor 34, an obstacle sensor 35, and a position information storage unit 36. The moving mechanism 33 is placed below the fourth operation unit 54 and moves the fourth operation unit 54. The position sensor 34 detects the position of the fourth operation unit 54. The obstacle sensor 35 detects an obstacle located in the traveling direction of the fourth operation unit 54. The position information storage unit 36 stores the position information of the fourth operation unit 54 detected by the position sensor 34, the position information of a plurality of use positions set in advance around the bed 10 at which the fourth operation unit 54 is used, and the like.

In addition, the peripheral unit moving unit 32 includes a drive control unit 37 and a power supply 38. The drive control unit 37 controls the moving mechanism 33 and the position information storage unit 36 based on the input information input from one of the first to third operation units 51 to 53, the position information of the third operation unit 53, the position information of the fourth operation unit 54 detected by the position sensor 34, and obstacle information detected by the obstacle sensor 35, which are output from the communication unit 542 of the fourth operation unit 54. The power supply 38 supplies power to the moving mechanism 33, the position sensor 34, the obstacle sensor 35, the position information storage unit 36, the drive control unit 37, and the fourth operation unit 54.

Figure 4:
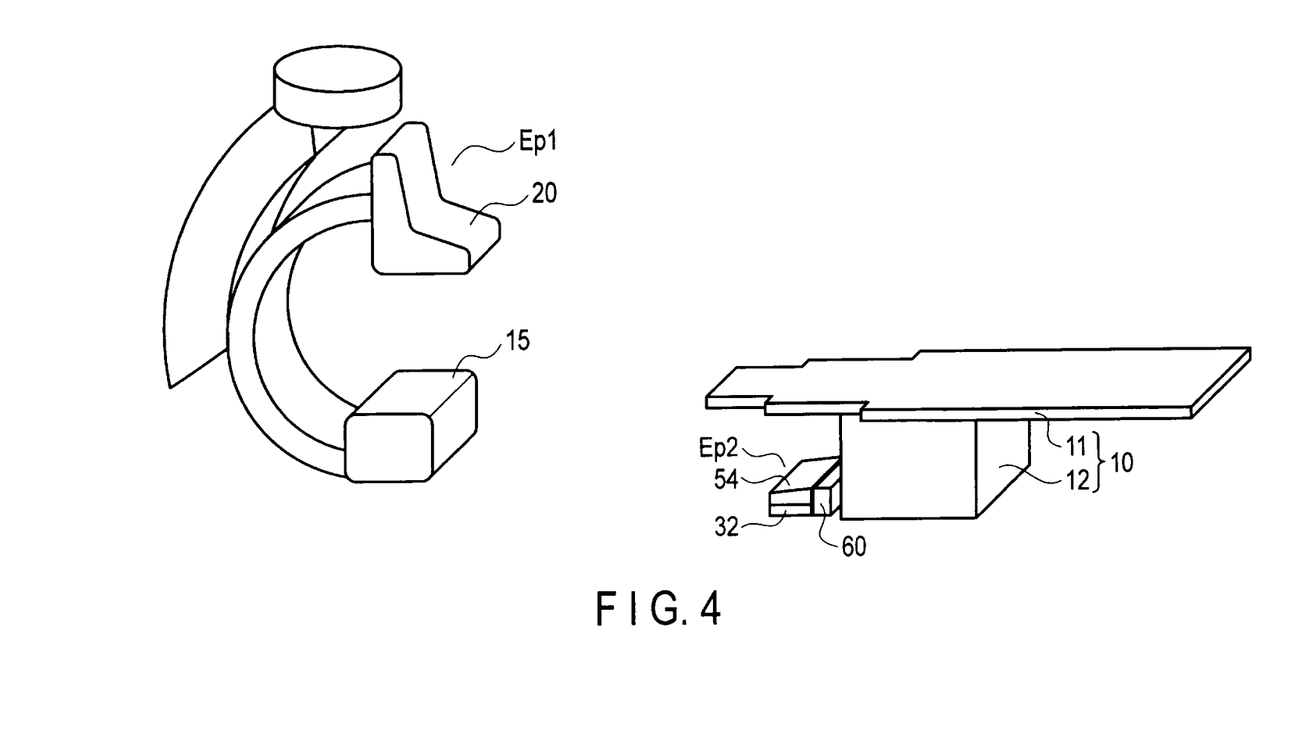
FIG. 4 is a view showing an example of the fourth operation unit which has moved to a retreat position, X-ray irradiation unit, and X-ray detection unit according to the embodiment.

The moving mechanism 33 includes a motor as a drive source, and causes the fourth operation unit 54 to linearly move and pivot. When the operator performs an input operation for interrupting or stopping the use of the fourth operation unit 54 by operating one of the first to third operation units 51 to 53, the moving mechanism 33 moves the unnecessary fourth operation unit 54 to a position where it does not interfere with an operation by the operator, for example, a retreat position Ep2 where the power supply 38 is located close to the charging unit 60 placed on the floor near the top support base 12 of the bed 10, as shown in FIG. 4.

Note that the moving mechanism 33 may move the fourth operation unit 54 to the retreat position Ep2 in accordance with an input from one of the first to third operation units 51 to 53 which moves the X-ray irradiation unit 15 and the X-ray detection unit 20 to the retreat position Ep1.

In addition, when the operator performs an input operation for starting the use of the fourth operation unit 54 after performing an input operation for selecting one of use positions corresponding to a plurality of pieces of position information stored in the position information storage unit 36 by using one of the first to third operation units 51 to 53, the moving mechanism 33 moves the fourth operation unit 54 at the retreat position Ep2 to the selected use position.

Figure 5:
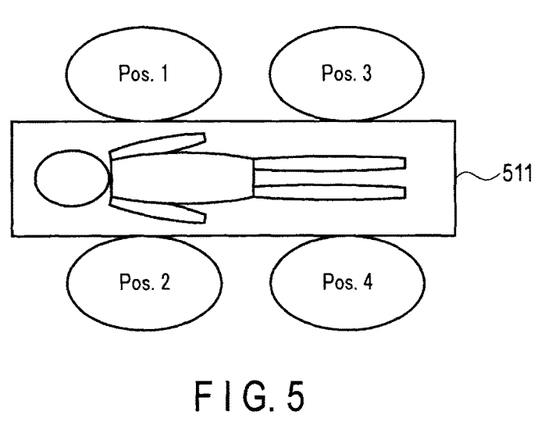
FIG. 5 is a view showing image data depicting a bed and an object displayed on the display panel of each of the first to third operation units and an example of each of positions corresponding to the use positions of the fourth operation unit relative to the bed.

In addition, as shown in FIG. 5, when the operator performs an input operation by using one of the first to third operation units 51 to 53 to select image data 511 depicting the bed 10 and the object P displayed on the display panel of each of the first to third operation units 51 to 53 and one of positions corresponding to use positions preset around the bed 10, e.g., "Pos. 1", "Pos. 2", "Pos. 3", and "Pos. 4", the moving mechanism 33 moves the fourth operation unit 54 at the retreat position Ep2 to the use position corresponding to the selected position.

The position sensor 34 includes a receiver which detects the magnetic field generated by a transmitter placed near the charging unit 60. The position sensor 34 then outputs position information indicating the position of the fourth operation unit 54 to the drive control unit 37. In addition, the obstacle sensor 35 detects an obstacle in the traveling direction of the fourth operation unit 54 or in a predetermined angular range relative to the traveling direction. The obstacle sensor 35 then outputs the information of the detected obstacle to the drive control unit 37.

The position information storage unit 36 stores preset position information corresponding to a plurality of use positions and the retreat position Ep2. The use positions include a "past use position including a moving path", a "use position for puncture", a "third operation unit position", a "past use position", and an "operator position". Selecting one of the plurality of use positions by performing an input operation using one of the first operation unit 51, the second operation unit 52, and the third operation unit 53 will stop the fourth operation unit 54 at the selected use position.

A "past use position including a moving path" is a use position including a moving path which is obtained by storing the position information detected by the position sensor 34 when the fourth operation unit 54 moves from the latest one of use positions selected in the past to the retreat position Ep2. When the operator selects a "past use position including a moving path", the moving mechanism 33 moves the fourth operation unit 54 from the retreat position Ep2 to the latest use position along the backward direction based on the position information of the use position including the moving path stored in the position information storage unit 36.

A "use position for puncture" is a use position corresponding to one of the positions on the upper right arm, upper left arm, right wrist, left wrist, right groin, left groin, right inferior limb, left inferior limb, and the like, each of which is the puncture position of the catheter inserted into the object P placed on the top 11 of the bed 10. Assume that the operator has selected a "use position for puncture". In this case, upon selecting one of a plurality of puncture positions in accordance with an input from one of the first operation unit 51, the second operation unit 52, and the third operation unit 53, the moving mechanism 33 stops the fourth operation unit 54 at a use position corresponding to the selected puncture position based on the position information of the use position corresponding to each puncture position stored in the position information storage unit 36.

A "third operation unit position" is a position near the third operation unit 53 whose position is changed for each examination or medical treatment. When the operator selects a "third operation unit position", the moving mechanism 33 then stops, based on the position information of the third operation unit 53, the fourth operation unit 54 at a position, as a use position, near the third operation unit 53 placed at the position indicated by the position information.

An "operator use position" is the position of the operator who operates the third operation unit 53. The moving mechanism 33 stops the fourth operation unit 54 at a position near the operator as a use position based on the position information of the operator having an accessory unit including a position sensor which detects the position of the operator and a communication unit which wirelessly transmits the position information of the operator which is detected by the position sensor to the fourth operation unit 54. Note that the accessory unit is a slipper which the operator wears in the imaging room, a foot band which the operator carriers, or the like.

Note that after the operator selects a use position, the moving mechanism 33 may move the fourth operation unit 54 at the retreat position Ep2 to the selected use position in accordance with an input from one of the first operation unit 51, the second operation unit 52, and the third operation unit 53 which moves the X-ray irradiation unit 15 and the X-ray detection unit 20 to an X-ray emission position.

Storing the information of a plurality of use positions in the position information storage unit 36 in advance in this manner can move the fourth operation unit 54 to various use positions in accordance with the types of examinations or medical treatments.

The drive control unit 37 controls the moving mechanism 33, the position information storage unit 36, and the power supply 38 based on input information from each of the first operation unit 51, the second operation unit 52, and the third operation unit 53, which is output from the system control unit 55 via the fourth operation unit 54. The drive control unit 37 moves the fourth operation unit 54 from one of each of the use position indicated by the position information stored in the position information storage unit 36, the use position near the third operation unit 53, and the use position near the operator and the retreat position Ep2 to the other position while avoiding the obstacles detected by the obstacle sensor 35 based on the position information detected by the position sensor 34 and the obstacle information detected by the obstacle sensor 35.

It is possible to hygienically move the fourth operation unit 54 without any manual operation by the operator because of unnecessity of touching by placing the peripheral unit moving unit 32 at the fourth operation unit 54 and moving the fourth operation unit 54 from one of a use position and the retreat position Ep2 to the other position. This reduces the moving operation by the operator to improve operability.

Note that if an alarm unit is provided and the fourth operation unit 54 cannot reach the other position due to an obstacle, the apparatus may generate an alarm sound or output alarm information to the system control unit 55 via the fourth operation unit 54 to display the information on the display unit 45. This makes it possible to notify the operator that the fourth operation unit 54 cannot reach the use position or the retreat position Ep2 because of an obstacle.

The power supply 38 includes a secondary battery 381 which supplies power to the moving mechanism 33, the position sensor 34, the obstacle sensor 35, the position information storage unit 36, the drive control unit 37, and the fourth operation unit 54. In addition, the power supply 38 includes a power receiving unit 382 which is located near the charging unit 60 at the retreat position Ep2 and recharges the secondary battery 381. The power receiving unit 382 of the power supply 38 then recharges the secondary battery 381 by receiving power from the charging unit 60 contactlessly by, for example, electromagnetic induction when the fourth operation unit 54 is at rest at the retreat position Ep2.

Providing the power supply 38 capable of recharging in this manner can reduce the floor area occupied by the fourth operation unit 54 because no power cable is required in the imaging room. This makes it possible to ensure a large floor area for the installation of various peripheral units around the bed 10 and a wide path for operators. When the fourth operation unit 54 is at rest at the retreat position Ep2, it is possible to move the fourth operation unit 54 to a use position so as to allow the operator to immediately use it when he/she wants to use, by recharging the secondary battery 381 as a drive source for the peripheral unit moving unit 32 and the fourth operation unit 54.

Note that the apparatus is provided with a unit moving unit having the same arrangement as that of the peripheral unit moving unit 32, which moves the injector 46 by moving in a self-propelled manner. In addition, a charging unit having the same arrangement as that of the charging unit 60 which supplies power for recharging the secondary battery of the unit moving unit is provided near the retreat position where the injector 46 is stopped when it is not necessary. When the unit moving unit moves the injector 46 from one of a use position and a retreat position to the other position by moving in a self-propelled manner and is at rest at the retreat position, the charging unit may supply power to recharge the secondary battery of the unit moving unit.

This makes it possible to hygienically move the injector 46 without bothering the operator. It is therefore possible to reduce the moving operation by the operator and improve operability. In addition, when the injector 46 is unnecessary and placed at the retreat position, it is possible to recharge a secondary battery serving as a drive source for the unit moving unit. The apparatus can move the injector 46 to a use position to allow the operator to immediately use it when he/she wants to use it.

In addition, the apparatus is provided with a communication unit which can perform wireless communication between the second operation unit 52 and the system control unit 55. The apparatus is also provided with a unit moving unit having the same arrangement as that of the peripheral unit moving unit 32, which moves the second operation unit 52 and the provided communication unit by moving in a self-propelled manner. In addition, a charging unit having the same arrangement as that of the charging unit 60 which supplies power for recharging the secondary battery of the unit moving unit is provided near the retreat position where the second operation unit 52 does not interfere with the operator when it is not necessary. When the unit moving unit moves the second operation unit 52 from one of a use position and a retreat position to the other position by moving in a self-propelled manner and is at rest at the retreat position, the charging unit may supply power to recharge the secondary battery of the unit moving unit.

This eliminates the necessity of a communication cable or power cable in the imaging room, and hence can reduce the floor area occupied by the second operation unit 52. In addition, this makes it possible to hygienically move the second operation unit 52 without bothering the operator. It is therefore possible to reduce the moving operation by the operator and improve operability. In addition, when the second operation unit 52 is unnecessary and placed at the retreat position, it is possible to recharge a secondary battery serving as a drive source for the second operation unit 52 and the unit moving unit. The apparatus can move the second operation unit 52 to a use position to allow the operator to immediately use it when he/she wants to use it.

According to the embodiment described above, enabling wireless communication between the fourth operation unit 54 and the system control unit 55 eliminates the necessity of a communication cable in the imaging room and can reduce the floor area occupied by the fourth operation unit 54. In addition, the peripheral unit moving unit 32 placed at the fourth operation unit 54 can move the fourth operation unit 54 from one of a use position and the retreat position Ep2 to the other position by moving in a self-propelled manner. This eliminates the necessity of touching, and hence can hygienically move the fourth operation unit 54 without bothering the operator.

In addition, when the fourth operation unit 54 is at rest at the retreat position Ep2, it is possible to recharge the secondary battery 381 serving as a drive source for the peripheral unit moving unit 32 and the fourth operation unit 54. This can move the fourth operation unit 54 to a use position to allow the operator to immediately use it when he/she wants to use it.

As described above, it is possible to reduce the operation by the operator and improve operability.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus, comprising:
   a top configured to move;
   a bed including the top;
   an X-ray tube configured to generate X-rays applied to an object placed on the top;
   a C-arm configured to hold the X-ray tube;
   a peripheral unit provided separately from the bed and the C-arm; and
   control processing circuitry configured to generate a control signal,
   wherein the peripheral unit includes a switch configured to input an instruction concerning an operation of the X-ray diagnostic apparatus and moves in a self-propelled manner by a motor to a position near an operator, and
   the control processing circuitry is further configured to generate a control signal for controlling the movement of the peripheral unit to the position near the operator.

2. The X-ray diagnostic apparatus according to claim 1, further comprising a secondary battery provided in the peripheral unit and configured to supply power to the motor; and
   charging circuitry provided at a retreat position below the bed and configured to supply power to the second battery when the peripheral unit is at the retreat position.

3. The X-ray diagnostic apparatus according to claim 1, wherein the switch is a foot switch configured to input an instruction from the operator.

4. The X-ray diagnostic apparatus according to claim 1, wherein the switch is configured to input the instruction concerning the operation of the X-ray diagnostic apparatus when operated by hand.

5. The X-ray diagnostic apparatus according to claim 1, further comprising an operation unit including input processing circuitry movably placed around the bed to input an instruction to move the top and the C-arm, a position sensor configured to detect a position of the input processing circuitry, and a wireless transmitter configured to transmit position information of the input processing circuitry to the peripheral unit,
   wherein the peripheral unit moves, by the motor, to a position near the operation unit based on movement information of the input processing circuitry.

6. The X-ray diagnostic apparatus according to claim 1, further comprising input processing circuitry configured to input a puncture position of a catheter inserted into the object placed on the top or a preset position.

7. The X-ray diagnostic apparatus according to claim 1, further comprising:
   input processing circuitry configured to input an instruction to move the top and movably placed around the bed;
   a position sensor placed on the operator who operates the input processing circuitry, the position sensor configured to detect a position of the operator; and
   a wireless transmitter configured to transmit position information of the operator to the peripheral unit,
   wherein the motor moves the peripheral unit to the position near the operator based on the position information of the operator.

8. The X-ray diagnostic apparatus according to claim 1, wherein the peripheral unit comprises a foot switch configured to input an instruction to perform X-ray emission from the X-ray tube and an instruction to stop a X-ray emission by foot operations and a wireless transmitter configured to transmit input information input from the foot switch.

9. An X-ray diagnostic apparatus, comprising:
a top configured to move;
a bed including the top;
an X-ray tube configured to generate X-rays applied to an object placed on the top;
a C-arm configured to hold the X-ray tube;
a peripheral unit provided separately from the bed and the C-arm;
control processing circuitry configured to generate a control signal;
image generation processing circuitry configured to generate an X-ray image based on the X-rays emitted by the X-ray tube and transmitted through the object; and
a sensor configured to detect a position of an operator,
wherein the peripheral unit comprises a display configured to display the X-ray image and moves in a self-propelled manner by a motor to the position of the operator, and
the control processing circuitry is further configured to generate a control signal for controlling the movement of the peripheral unit to the position near the operator.

10. A foot switch provided separately from a bed and a C-arm included in an X-ray diagnostic apparatus and configured to input an instruction concerning an operation of the X-ray diagnostic apparatus comprising:
a receiver configured to receive a control signal from the X-ray diagnostic apparatus;
a motor configured to move in a self-propelled manner to a position near an operator of the X-ray diagnostic apparatus; and
control processing circuitry configured to generate a control signal for controlling the motor to move to the position near the operator.

11. The foot switch according to claim 10, further comprising a secondary battery configured to supply power to the motor,
wherein the control processing circuitry is further configured to control the motor to move to a position where the secondary battery is connected to the charging circuitry provided at a retreat position below the bed.

12. The foot switch according to claim 10, further comprising an obstacle sensor configured to detect an obstacle,
wherein the control processing circuitry is further configured to control the motor to move while avoiding the obstacle detected by the obstacle sensor.

13. The foot switch according to claim 10, further comprising a transmitter/receiver configured to communicate position information with the X-ray diagnostic apparatus,
wherein the control processing circuitry is further configured to control the motor to move to the position near the operator based on the position information received by the transmitter/receiver.

* * * * *